Figure 1:
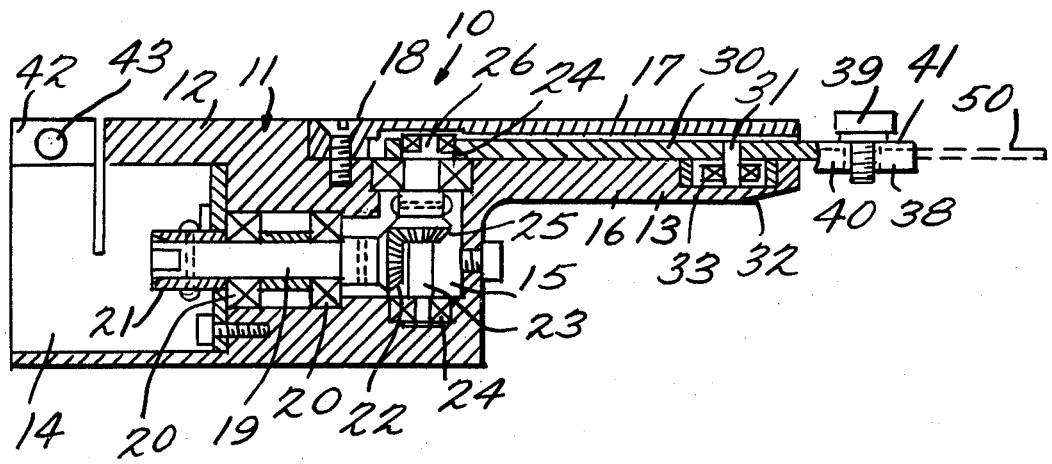

United States Patent [19]
Tuke

[11] 3,977,289
[45] Aug. 31, 1976

[54] SAWS AND BLADES THEREFOR

[75] Inventor: Michael Anthony Tuke, Sutton, England

[73] Assignee: National Research Development Corporation, London, England

[22] Filed: Apr. 24, 1975

[21] Appl. No.: 571,397

Related U.S. Application Data
[62] Division of Ser. No. 431,554, Jan. 7, 1974.

[30] Foreign Application Priority Data
Jan. 8, 1973 United Kingdom................. 1004/73
July 13, 1973 United Kingdom............... 33565/73

[52] U.S. Cl. .................................... 83/835; 83/697; 83/698; 30/392; 145/31 AB
[51] Int. Cl.² ......................................... B27B 33/02
[58] Field of Search..................... 83/835, 698, 697; 30/392; 145/35 E, 108 R, 108 A, 108 B, 31 R, 31 AB

[56] References Cited
UNITED STATES PATENTS

| | | | |
|---|---|---|---|
| 709,857 | 9/1902 | Anderson ....................... | 145/31 AB |
| 942,920 | 12/1909 | Martin............................ | 145/31 AB |
| 2,747,631 | 5/1956 | Behlefeldt ...................... | 145/108 B |
| 2,849,039 | 8/1958 | Dreier............................. | 145/31 R |
| 2,904,373 | 9/1959 | Dowdy et al.................... | 145/108 R |
| 2,987,086 | 6/1961 | Westlund........................ | 83/835 |
| 3,477,479 | 11/1969 | Doty............................... | 83/835 |

Primary Examiner—Donald R. Schran
Attorney, Agent, or Firm—Cushman, Darby & Cushman

[57] ABSTRACT

A powered saw developed for use in orthopaedic surgery has a strip-form blade carrier projecting from a casing in which it is driven at its inner end in an orbiting manner while further towards the carrier free end the carrier is constrained to allow longitudinal translation and pivotal movement. In consequence, the free end of the carrier, and all points of a blade projecting therefrom, are also subjected to an orbital motion. By appropriate location of teeth the blade can therefore cut in any combination of both sideways directions and also at its tip, and preferably has non-symmetrical teeth which are all raked in the same sense around the edge of the blade.

2 Claims, 10 Drawing Figures

U.S. Patent  Aug. 31, 1976  Sheet 2 of 2  3,977,289
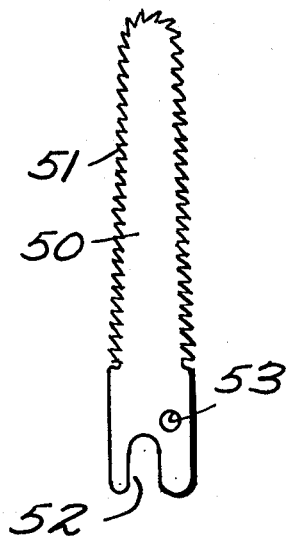
Fig. 3.
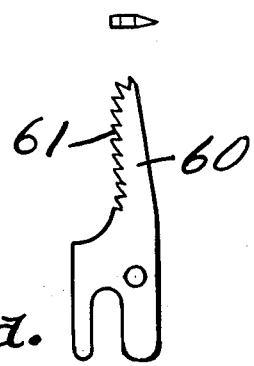
Fig. 4a. Fig. 4b.
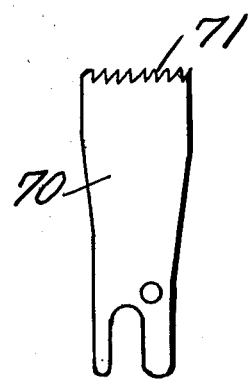
Fig. 5a. Fig. 5b.
 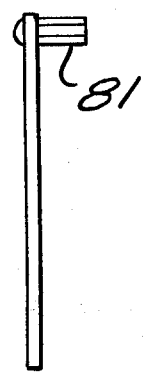 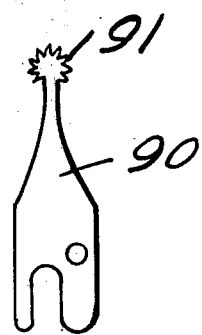
Fig. 6a. Fig. 6b. Fig. 7.

SAWS AND BLADES THEREFOR

This is a division of application Ser. No. 431,554 filed Jan. 7, 1974.

This invention concerns saws and blades therefor, and more particularly, but not exclusively, power-operated saws suited to use for cutting bone during orthopaedic surgery. The invention has, in fact, been developed for this last purpose and, for convenience will be described hereinafter in this context. However, it will be appreciated that the invention may find other useful applications.

Saws employed for the purpose in question are conventionally of two kinds: those in which the blade is toothed along at least one or both side edges and is reciprocated longitudinally to effect a cutting action, and those in which the blade is toothed across its outermost free end edge and is reciprocated transversely. Both of these kinds of saw are, of course, of equivalent operation in that the blade is toothed along a single direction and is reciprocated in this direction; and the provision of side or end cutting saws simply takes account of the different circumstances which can arise in respect of access to bones which are to be cut and the dimensions and geometry of the required cuts. Nevertheless, the two kinds of saw are normally different in that conventional practice is to use a common power unit with a range of tool accessories, and the latter includes two saw accessories to apply the power unit section in respectively different manner to the associated blades. Also, two different blade forms are involved by virtue of the different location of toothing.

According to the present invention there is provided a saw comprising: a rotary drive member; an elongate blade-carrying mechanism having a first end portion, an intermediate portion, and a second end portion, said first end portion being coupled for rotation with said drive member in orbital manner relative to the axis of rotation of said drive member; and a casing housing said drive member and said first end and intermediate portions of said blade mechanism, said blade mechanism intermediate portion being effectively constrained by said casing for longitudinal sliding and pivotal movement in a plane parallel to that of said orbital rotation. In this context, it is to be understood that the blade-carrying mechanism comprises a carrier for a generally strip form blade, or such a carrier and blade in combination.

In another aspect the present invention provides a saw blade of elongate, generally strip form having a plurality of similarly non-symmetrical teeth in a sequence around or across at least one end portion thereof.

In yet another aspect the present invention provides a saw blade of elongate, generally strip form having a plurality of teeth extending along both side edges and one end edge thereof.

Figure 2:
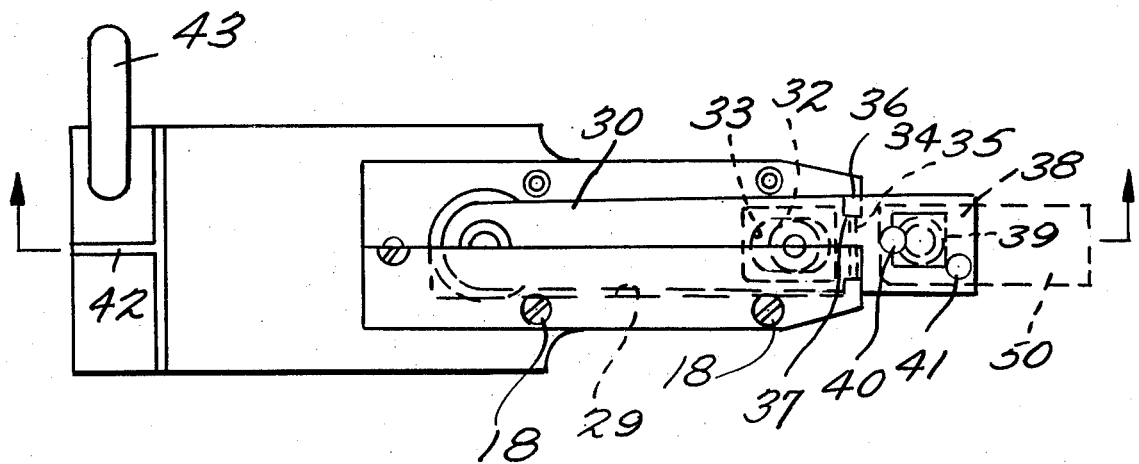

For a clearer understanding of these aspects of the invention, the same will now be described by way of example with reference to the accompanying drawings, in which:

FIGS. 1 and 2 respectively illustrate in partly sectioned side elevation and plan views of one embodiment of a saw and blade according to the invention, and FIGS. 3 to 7 respectively illustrate different embodiments of blades according to the invention.

The illustrated saw is denoted generally at 10 and comprises a casing 11 having a tubular main body portion 12 extending axially from one side thereof into a flat nose portion 13. The casing main body 12 is axially hollowed at 14 from its free end in stepped manner and is similarly diametrally hollowed at 15 from a position adjacent the nose portion 13. The nose portion is formed in a hollowed two-part construction of which a radially inner part 16 is integrally formed with the main body 12, and a radially outer part 17 is a separate plate which extends partway over the main body and is secured by screws 18.

The axially hollowed portion 14 of the main body coaxially houses a first drive shaft 19 journalled in two bearings 20 adjacent respectively opposite ends of the shaft, and end of the shaft nearer the free end of the main body being formed as, or carrying, a drive coupling member 21, and the other end of the shaft carrying a first bevel gear wheel 22. The coupling member 21 is of a conventional form, such as a plug having a laterally-tapered axially-diametral slot therein, as used for connection with a rotary drive coupling socket of a pneumatically-powered motor unit.

The main body diametral hollow 15 axially houses a second drive shaft 23 journalled in two bearings 24 respectively located at the inner end and partway towards the outer end of the shaft. Between the bearings 24 the shaft 23 carries a second bevel gear wheel 25 meshed with the first such wheel 22. At its outer end the shaft 23 is reduced to form an eccentric drive spindle 26 which is journalled in a bearing 27 spaced from the adjacent one of bearings 24 by a collar 28.

The hollow of the nose portion 13 is denoted at 29 and is of flat elongate form extending from one end where it communicates with the main body diametral hollow 15 to receive the drive spindle 26 and associated bearing 27, to the other end where it opens into the free end of the nose portion 13. This nose hollow 29 receives a bar-like blade carrier 30 therein, the carrier being apertured at its inner end to receive the spindle 26 and associated bearing 27. The carrier 30 is also formed with an aperture partway towards its outer end to receive a guide spindle 31. The spindle 31 projects from the carrier 30 and is journalled in a bearing 32 located in a guide well 33 formed in the nose portion part 16 for axial sliding and rotation. Further towards its outer end, the carrier 30 is formed with like opposed notches 34 in its sides, which notches are communicated by a bore 35 through the carrier. These notches receive respective sealing blocks 36 in the manner of pistons, the blocks 36 both being held in engagement with the adjacent surfaces of the nose portion cavity 29 by a rod 37 passing through the bore 35.

The outer end of the carrier 30 is relieved from below and its end edge to receive a blade locking plate 38. The carrier 30 is bored, and the plate 38 is bored and threaded, for securement of the latter to the former by a bolt 39. Also, two blade locating pins 40 and 41 project from the carrier 30 towards the plate 38 which is bored to receive the pins. The bolt 39 and pin 40 are located in longitudinal alignment relative to the carrier but are off-set to one side of the medial plane of the saw, with the pin 40 being rearward of the bolt 39, while the pin 41 is off-set to the other side of the medial plane of the saw and is forward of the bolt. Also, the pin 40 extends wholly through the plate 38, but the pin 41 only extends partway through the plate and has its free end chamfered to be shortest nearest the free end of the carrier 30.

The plate 38, bolt 39 and pins 40, 41, serve to locate and clamp to the carrier 30 a blade of which one embodiment is denoted in ghost form at 50 and, for convenience, will be described with reference to FIG. 3. The blade 50 is of elongate, generally strip form tapered towards one end which is rounded. The blade is toothed along major portions of both side edges leading from the rounded end, and also around such end, the toothing being in a single continuous sequence and composed of similar non-symmetrically raked teeth 51 having a triangular profile. It is to be noted that the raking is in the same sense around the blade for all of the teeth.

At its untoothed end the blade is formed with a longitudinal slot 52 off-set to one side of the longitudinal central axis of the blade, and a round hole 53 off-set to the other side of the axis. This end of the blade is dimensioned and formed for receipt in a predetermined disposition between the carrier 30 and the plate 38, with the blade slot 52 located around the bolt 39 and pin 40, and the hole 53 around the pin 41. The plate 38 need not be completely removed from the carrier 30 to locate the blade since the slot 52 can pass around the bolt 39 and pin 40, and the blade can pass over pin 41 until the hole 53 snaps around the same.

In use of the illustrated saw the casing 11 is connected with a rotary power unit of the aforementioned pneumatic kind by receipt of the relevant drive coupling socket in engagement wih the coupling plug member 21. In order to secure such engagement the adjacent casing main body portion is longitudinally split at 42, and bored and tapped to receive a clamp bolt 43.

Application of rotary power to the coupling plug member 21 rotates the second drive shaft 23 through the first drive shaft 19 and bevel gear wheels 22 and 25, and so rotates the drive spindle 26 in orbital manner about the longitudinal axis of rotation of the shaft 23. This orbital motion is applied through the drive spindle bearing 27 to the inner end of the carrier 30. The intermediate portion of the carrier 30 is constrained by the guide spindle 31, bearing 32, and well 33, to longitudinal sliding and pivotal motion in the plane of the casing nose portion hollow 29, and in consequence the outer end portion of the carrier 30 and also the blade 50 are subjected to a generally corresponding orbital motion of opposite sense to that of the drive spindle 26. In particular, this is true for each tooth 51 of the blade, with each tooth motion being of an orbital size and shape which depends on its location relative to the drive spindle 26 and guide spindle 31. In this last respect it is to be noted that the motion of a tooth is the same as that of the drive spindle in respect of longitudinal component, but proportional in respect of lateral component. Generally speaking the individual tooth motion will be that of an elliptical orbit, but it can be circular.

Also, generally speaking, it is sufficient for an intermediate portion of the carrier 30 to be constrained to a lesser lateral motion than that of the primary orbit to provide the relevant effectively pivotal function. In practice, if the primary orbit is small, the constraining guide spindle 31 and its bearing 32 need only be located in the well 33 for longitudinal sliding relative to the carrier 30, other necessary motions being possible within the relevant guide spindle-bearing engagement and the bearing construction.

In any event, since each tooth is orbited, it will be appreciated that each tooth can cut into an adjacent object during one half cycle of its orbit and withdraw from the object during the other half cycle. Moreover, the orientation of these half cycles relative to their orbits, and therefore to the primary orbit of the spindle 25, varies in dependence upon the position of the tooth on the blade; and the configuration of the tooth, with particular reference to the cutting portion orientation relative to the blade, is chosen accordingly. It is for this reason that the teeth are each of similar form relative to the respective adjacent portion of the blade and it will be appreciated that, in the result, the blade 50 will cut with similar effect if urged to one side or the other against, or longitudinally into, an object without any change of drive motion or blade being necessary. This facility is particularly advantageous for cutting bone during orthopaedic surgery when different cutting modes are required, often within restricted acess, and the saving in time otherwise employed in changing between different saw tool accessories is also advantageous.

It is to be noted that the practical benefits of the invention, as applied to a hand-held orthopaedic or other saw, only arise at high speed operation, in an approximate range of ten to twenty thousand revolutions per minute, since at lower speeds the relevant small orbital motion is applied to the user's hand rather than the blade. It is for this reason that associated use of a pneumatically-powered motor unit is preferred.

Additional advantage arises from the provision of the piston-like blocks 36 which serve to seal the casing against ingress of foreign material. The form of the blade attachment mechanism is also advantageous in that, if the carrier plate is insufficiently screwed down after insertion of a blade, the bolt 39 and the pins 40 and 41 act against undesirable lateral movement of the blade in its cutting plane, and the pin 41 acts against complete separation of the blade from the carrier. Moreover, it is to be noted that the blade can only be entered fully into the carrier in one disposition, and this ensures that the blade teeth are correctly orientated in relation to the primary orbital motion of the drive spindle 26.

While the invention has been more specifically described in relation to the illustrated embodiment of FIGS. 1 to 3, it is not intended to be limited thereby and is capable of variation within the initial broader discussion thereof hereinbefore. This is particularly so of the form of blade since, although the invention affords the provision of a 'general purpose' saw for orthopaedic use, the relevant orbital motion can be usefully applied to other special-purpose blade forms. For example, FIG. 4 illustrates in plan and end elevation views (a) and (b) a blade 60 having a succession of teeth 61 along only one side and across the tip thereof, the blade being of tapered sectional form converging away from the toothed side. FIG. 5 similarly illustrates a blade 70 having a dished and laterally enlarged end portion 71 which is toothed at 72 across its outermost end periphery to form a saw gouge. FIG. 6 illustrates in plan and side elevation views another 'blade' 80 in which the strip part of the blade is not toothed but has, projecting orthogonally from one side of its free end portion a cylindrical cutter 81 with a succession of teeth circumferentially therearound, which teeth individually extend longitudinally along the cutter from its free end.

FIG. 7 illustrates in plan view a blade 90 in which the strip is convergently tapered towards its free end where it terminates in an enlarged disc toothed around its periphery.

I claim:

1. A saw blade of strip form having a plurality of teeth extending in a sequence at least along both side edges and one end edge thereof, said teeth each being of nonsymmetrical form raked in a common direction around the blade.

2. A blade according to claim 1 which is longitudinally slotted in laterally off-set manner at its other end from said one end, and is formed with a hole adjacent said slot but laterally off-set in the opposite sense from said slot.

* * * * *